United States Patent
Aetukuri et al.

(10) Patent No.: US 10,247,701 B2
(45) Date of Patent: Apr. 2, 2019

(54) DISSOLVED-OXYGEN SENSOR UTILIZING IONIC OXYGEN MOTION

(71) Applicant: INTERNATIONAL BUSINESS MACHINES CORPORATION, Armonk, NY (US)

(72) Inventors: Naga Phani B. Aetukuri, San Jose, CA (US); Stuart S. P. Parkin, San Jose, CA (US); Mahesh G. Samant, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 265 days.

(21) Appl. No.: 15/195,731

(22) Filed: Jun. 28, 2016

(65) Prior Publication Data
US 2017/0370879 A1    Dec. 28, 2017

(51) Int. Cl.
H01M 12/06 (2006.01)
G01N 27/49 (2006.01)
G01N 27/327 (2006.01)
G01N 27/404 (2006.01)

(52) U.S. Cl.
CPC ........... *G01N 27/49* (2013.01); *G01N 27/327* (2013.01); *G01N 27/404* (2013.01)

(58) Field of Classification Search
CPC .................................................. H01M 12/06
USPC ..................................................... 205/785.5
See application file for complete search history.

(56) References Cited

U.S. PATENT DOCUMENTS

| | | | |
|---|---|---|---|
| 6,551,386 B2 | 4/2003 | Weiler | |
| 6,592,782 B2 | 7/2003 | MacKay et al. | |
| 6,767,663 B2 | 7/2004 | Li et al. | |
| 7,048,844 B2 * | 5/2006 | Chen | G01N 27/419 204/426 |
| 7,211,345 B2 | 5/2007 | Hampden-Sm et al. | |
| 8,500,874 B2 | 8/2013 | Tabata et al. | |
| 8,728,214 B2 | 5/2014 | Maurer | |

(Continued)

FOREIGN PATENT DOCUMENTS

CN    1253849 A    5/2000

OTHER PUBLICATIONS

Jeong et al.,"Suppression of Metal-Insulator Transition in VO2 by Electric-Field Induced Oxygen Vacancy Formation", Science, vol. 339, pp. 1402-1405, 2013.

(Continued)

*Primary Examiner* — Zulmariam Mendez
(74) *Attorney, Agent, or Firm* — Daniel E. Johnson

(57) ABSTRACT

An apparatus includes an oxide layer having ion transport channels that facilitate the migration of oxygen ions from a first side to a second side of the layer. Specifically, molecular oxygen is decomposed into oxygen ions at the first side, and oxygen ions recombine into molecular oxygen at the second side. The apparatus includes a first chamber having a polarizable medium located on the second side of the oxide layer; a second chamber having an analyte that includes dissolved oxygen is located on the first side. The apparatus further includes a gate electrode that is in contact with, and applies a voltage to, the polarizable medium; in this manner, an electric field is applied to the second side of the oxide layer, which drives oxygen ions across the oxide layer. The apparatus can be used as an oxygen sensor, e.g., for detecting oxygen in a liquid such as blood.

14 Claims, 9 Drawing Sheets

(56) References Cited

U.S. PATENT DOCUMENTS

| | | | |
|---|---|---|---|
| 2003/0121801 A1* | 7/2003 | Inaba | G01N 27/4075 205/785.5 |
| 2003/0188637 A1 | 10/2003 | Ito et al. | |
| 2014/0030510 A1 | 1/2014 | Kimura et al. | |
| 2015/0129431 A1 | 5/2015 | Winther-Jensen et al. | |

OTHER PUBLICATIONS

Altendorf et al., "Facet-independent Electric-Field-induced vol. Metallization of Tungsten Trioxide Films", Advanced Materials, vol. 28, pp. 5284-5292, 2016.

Li et al., "Suppression of Ionic Liquid Gate-Induced Metallization of SrTiO3(001) by oxygen", ACS Nano, vol. 13, pp. 4675-4678, 2013.

Chueh et al., "Electrochemistry of Mixed Oxygen Ion and Electron Conducting Electrodes in Solid Electrolyte Cells", Annual Rev. Chem. Biomol. Eng., vol. 3, pp. 313-341, 2012.

\* cited by examiner

DISSOLVED-OXYGEN SENSOR UTILIZING IONIC OXYGEN MOTION

TECHNICAL FIELD

This invention relates to a device that senses oxygen dissolved in a liquid medium such as blood, by utilizing ionic liquid gate induced oxygen ion motion and the consequent change in conductivity of an oxide film.

BACKGROUND

Controlling the transport and structural properties of oxide thin films through various parameters (such as temperature, strain, and electric field) makes them useful for technological applications including sensor, memory and logic devices. Recently, a mechanism was demonstrated for controlling the properties of a class of oxide materials, namely, gating them with ionic liquids. The voltage gating of an ionic liquid (IL) at the surface of an oxide film can create an electric field large enough that oxygen migrates from within the interior of the film to its surface, as illustrated in FIG. 1. This process is reversible and can be used with a large class of oxides having channels through which oxygen ions migrate. Such an ion transport channel is a collection of lattice sites along which oxygen ion diffusion occurs, as opposed to diffusion through one or more mesoscopic pores.

Of particular interest are the oxides $VO_2$ and $WO_3$, which can be reversibly gated for thicknesses at least as large as ~120 nm. One consequence of the IL gating is the change in conductivity of the oxide films. In particular, for $VO_2$, which displays a metal to insulator transition (MIT) near room temperature, one observes a suppression of this MIT even at low temperatures. The observed conductivity increase of the insulating state upon IL gating (application of positive gate voltage) is roughly three orders of magnitude and is non-volatile (see Jeong et al., "Suppression of metal-insulator transition in $VO_2$ by electric-field induced oxygen vacancy formation", Science, vol. 339, pp. 1402-1405, 2013). The material retains its conducting properties even when the bias voltage is reduced to zero and, further, even after the removal of the ionic liquid. The original high resistance state of the pristine material can be reached upon application of a reverse gate voltage (negative gate voltage). Upon IL gating (application of a positive gate voltage) in the case of $WO_3$, which is a band insulator, one observes an increase in conductance of almost six orders of magnitude (see Altendorf et al., "Facet-independent electric-field-induced volume metallization of tungsten trioxide films", Advanced Materials, 2016). For both of these oxides, the original insulating state is reached during reverse gating by migration of oxygen from the surface of the film and/or the ionic liquid to its interior. FIG. 2 shows an IL gating effect for a 10 nm $VO_2$ thin film. The pristine film shows an MIT characteristic of $VO_2$, which is suppressed by IL gating due to the creation of oxygen vacancies.

One observes a clear correlation between the increased conductivity of the film and the removal of oxygen from the film, while the converse is also true. In particular, the film conductivity depends on the oxygen present in the environment during the IL gating process. The presence of a sufficiently high concentration of oxygen can completely suppress any gate-induced conductivity increase (see FIG. 3). Other gases including nitrogen or argon have no significant effect on the IL gating process (see Li et al., "Suppression of ionic liquid gate-induced metallization of $SrTiO_3$ (001) by oxygen", ACS Nano, vol. 13, pp. 4675-4678, 2013). This is evidence of an extremely high specificity of the IL gating process to oxygen.

The precise measurement of the oxygen concentration in a liquid medium is routinely necessary for applications in several industries such as medicine, biopharmaceutics, and the food and beverage industries. For example, the measurement of the amount of oxygen that is dissolved in blood (which is less than or equal to the oxygen saturation limit in blood) is critical for the diagnosis of several respiratory illnesses. The measurement of oxygen dissolved in a liquid requires an apparatus that separates oxygen from the sample being analyzed (known as the analyte) and then transports the separated oxygen to a measurement device. For example, in polarography (a widely used technique for the measurement of dissolved oxygen), oxygen from the analyte is transported through an oxygen-permeable membrane to an electrochemical cell. In the cell, reduction of oxygen results in a thermodynamically defined polarization voltage at a constant measurement current. The polarization voltage is directly correlated with the oxygen concentration and therefore the output voltage of the sensor is a measure of the oxygen in the analyte. However, these sensors are costly since platinum or gold electrodes are required as the working electrodes. Also, the requirement to build an electrochemical cell with reference electrodes for precise voltage measurement makes them bulky.

SUMMARY

The IL gate induced transport of oxygen across an oxide film and the concomitant change in conductivity of the oxide film can be utilized in several technological applications. This gate-induced migration of oxygen in and out of an oxide film, and the accompanying conductivity changes, give rise to the utility of such an oxide film in an oxygen sensing device. Herein are described sensing devices that utilize the principle of ionic liquid gate driven oxygen ion motion to detect dissolved oxygen in a liquid medium.

One embodiment of the invention is an apparatus that includes an oxide layer having ion transport channels, in which the channels facilitate the migration of oxygen ions from a first side of the layer to a second side of the layer. The apparatus includes a first chamber having a polarizable medium located on the second side of the oxide layer; a second chamber having an analyte that includes dissolved oxygen is located on the first side of the oxide layer. The apparatus further includes a gate electrode that is in contact with, and applies a voltage to, the polarizable medium; in this manner, an electric field is applied to the second side of the oxide layer, which drives oxygen ions across the oxide layer. Specifically, molecular oxygen is decomposed into oxygen ions at the first side of the oxide layer, and oxygen ions recombine into molecular oxygen at the second side of the oxide layer. The oxide layer preferably has an electronic resistivity of <1 mΩ-cm when the electric field is applied to the second side of the oxide layer, and preferably has a thickness of greater than 10 nm and less than 1 μm. The electric field is preferably greater than 10 MV/m. The polarizable medium may be an ionic liquid, an ionic gel and/or a molten salt.

In one aspect of the invention, the apparatus is used as an oxygen sensor, e.g., for detecting oxygen in a liquid such as blood.

DETAILED DESCRIPTION

A device for sensing dissolved oxygen is described that utilizes oxygen ion motion induced in an ionic-liquid gated metal oxide thin film in contact with an analyte having dissolved oxygen whose concentration is to be measured. The oxygen ion current across a metal oxide thin film (such as $WO_3$, $VO_2$ or $TiO_2$) is dependent on the oxygen concentration in the analyte and the voltage applied to the ionic liquid gate. The functional layer needs no precious metals such as Pt, Au or Ag and is amenable to being incorporated into micron-scaled sensors. This permits the construction of sensors having a substantial reduction in size and cost. Moreover, such a sensor may be advantageously portable and/or battery operated.

Oxygen Ion Transport Theory

First, we assume that oxygen-ion transport is driven by the vacancy mechanism. Vacancy formation and annihilation reactions are given by the following equilibrium equation (Kröger-Vink notation is used) where all the symbols have their usual meaning.

$$\tfrac{1}{2}O_2 + V_{\ddot{O}} \leftrightarrow O_O^x + 2h \qquad (1)$$

Here $V_{\ddot{O}}$ represents a doubly-ionized oxygen vacancy, h represents a hole, and $O_O^x$ represents an oxygen ion on the oxygen lattice site.

Figure 4:
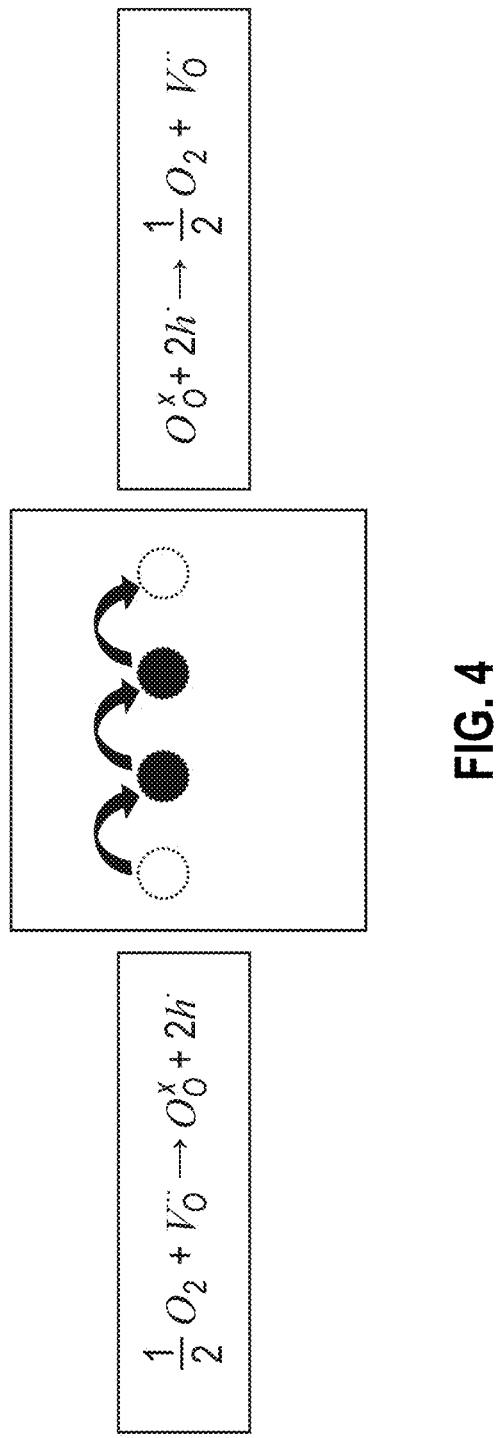
FIG. 4 is a schematic of the oxygen vacancy transport in an oxygen-ion conductor. It is assumed that the composition and/or potential differences are such that the oxygen vacancies move from left to right in the diagram. In this figure and others herein, filled circles represent an oxygen ion in the lattice of the oxide layer, whereas open circles represent oxygen vacancies.

In the oxide thin films of interest to the applications and embodiments of this invention (such as $VO_2$ and $WO_3$), there is enough electronic conductivity that the electrochemical vacancy formation and annihilation reactions occur on the surfaces of the oxide thin film, as shown schematically in FIG. 4.

The transport of oxygen-ions in oxide materials is usually mediated by oxygen vacancy diffusion. In the absence of an electric field, $\vec{E}=0$, the oxygen ionic diffusion is a thermally activated process and is given by:

$$D_{\vec{E}=0} = D_0 e^{-U/kT} \qquad (2)$$

In the above equation, $D_{\vec{E}=0}$ is the diffusivity at $\vec{E}=0$, U is the activation barrier for vacancy hopping, k is the Boltzmann constant, and T is the temperature. It is generally assumed that the electric fields available for the drift of oxygen vacancies are small enough that the diffusion coefficient is independent of electric field. In the case of IL gating, the electric fields are intense enough that the diffusion constant is no longer independent of the electric field. In preferred embodiments of this invention, fast-ion transport at room temperature is achieved by applying large electric fields via ionic liquids at or near room temperature. An increase in temperature increases the diffusive current of oxygen vacancies. In the next section, the theory for diffusion at large electric fields is outlined.

Diffusion in an Electric Field

Figure 5:
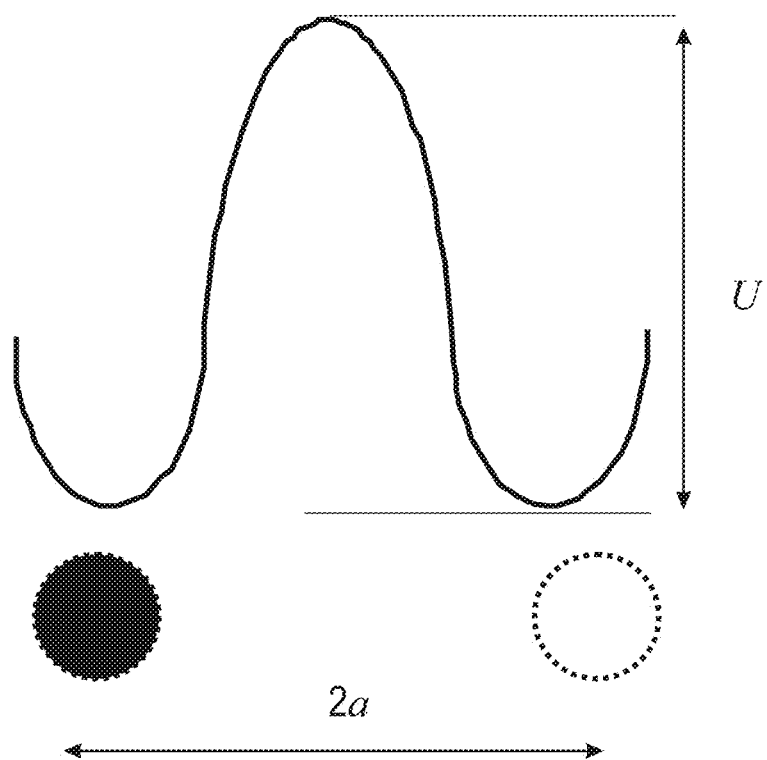
FIG. 5. Potential Energy around an oxygen vacancy in the absence of an electric field. U is the activation barrier for vacancy hopping in a lattice.
Figure 6:
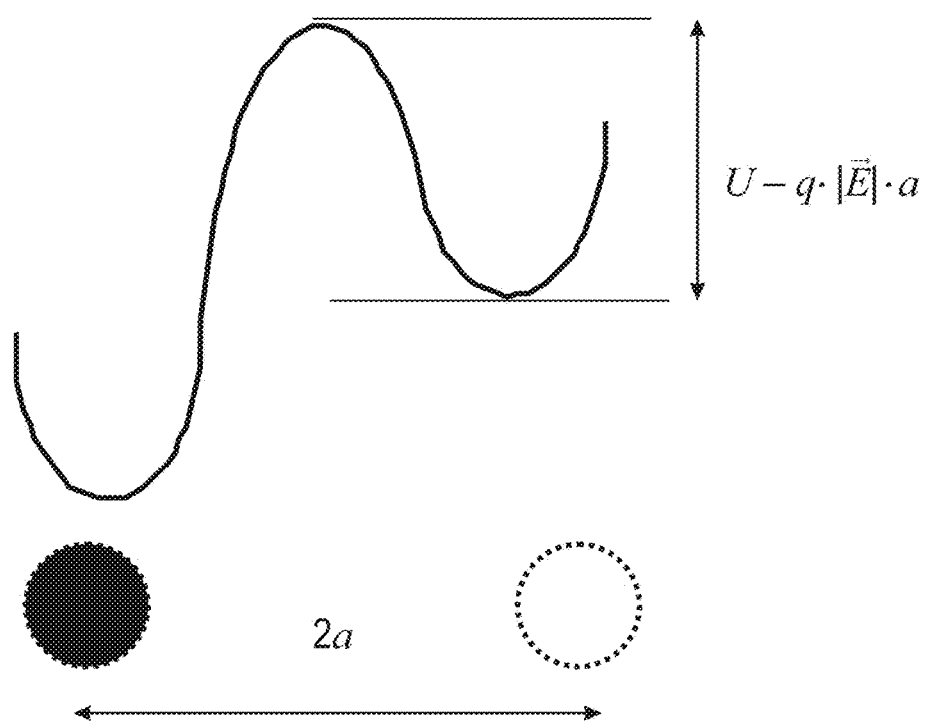
FIG. 6. Potential Energy U around a vacancy in the presence of an electric field, $\vec{E}$. The activation barrier for vacancy hopping in a lattice is decreased by the quantity $q \cdot |\vec{E}| \cdot a$.

First, we consider the potential energy landscape of an oxygen vacancy in an oxygen ion lattice. The barrier to the hopping of an oxygen vacancy across the shortest jump distance of 2a is the activation energy U (see FIG. 5). Upon the application of a positive electric field (see FIG. 6), the potential barrier is skewed to favor the forward (left to right) jump of the oxygen ion (or the backward jump of the oxygen vacancy). This is equivalent to the lowering of the energy barrier by the quantity $q \cdot |\vec{E}| \cdot a$, where q is the charge on the defect, $\vec{E}$ is the electric field, and 2a is the shortest jump distance. The decreased activation barrier in the presence of an electric field increases the diffusivity at any given temperature. This can be written as:

$$D = D_0 e^{(-U + q \cdot |\vec{E}| \cdot a)/kT} = D_{\vec{E}=0} \cdot e^{(q \cdot |\vec{E}| \cdot a)/kT} \qquad (3)$$

Figure 7:
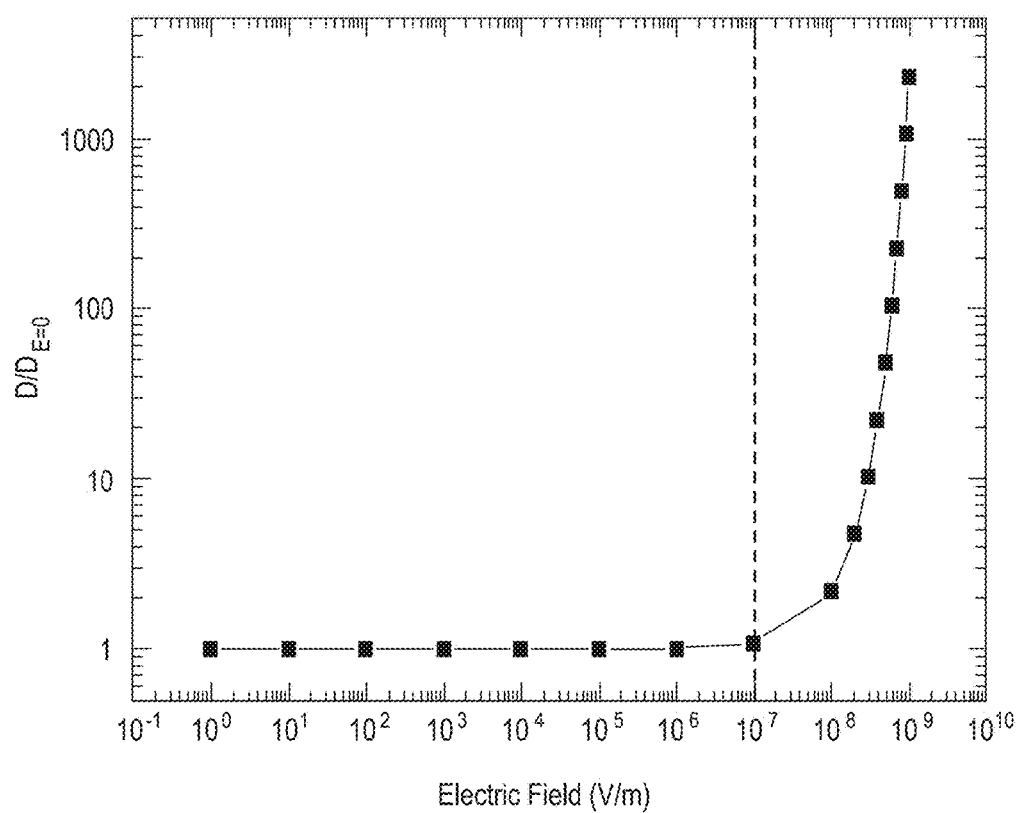
FIG. 7. Plot of diffusivity enhancement with electric field. At high electric fields ($>10^7$ V/m), there is a rapid increase in the diffusivity when compared to the zero-field diffusivity.

Clearly, the term $e^{(q \cdot |\vec{E}| \cdot a)/kT}$ implies that the diffusivity enhancement is exponential with respect to electric field strength. This enhancement in diffusivity for oxygen vacancy diffusion in the presence of an electric field is plotted in FIG. 7. There is a giant enhancement in the diffusivity at electric fields above $10^7$ V/m. By using ionic liquids, interfacial electric fields $>10^8$ V/m are easily possible within the electrical double layer, and therefore these large electric field regimes can be generated using relatively small voltages (e.g., 1-3 V).

The electrical double layer is formed at the interface between a polarizable medium and a metallic electrode. The surface charges on a metallic electrode, which can be controlled by the application of an electric potential, electrostatically attract ions of opposite charge present in the polarizable medium. The layer of surface charge on the metallic electrode and the layer of ions of the medium together form the double layer. The double layer of charges can be viewed as a parallel plate capacitor, in which the distance between the plates is determined by the ionic size, or in the case of electrolyte solutions, by the size of the ionic solvate. It is assumed that the interaction is predominantly electrostatic and that negligible electrochemical reactions occur.

Preferred Embodiments and Methods

Figure 8:
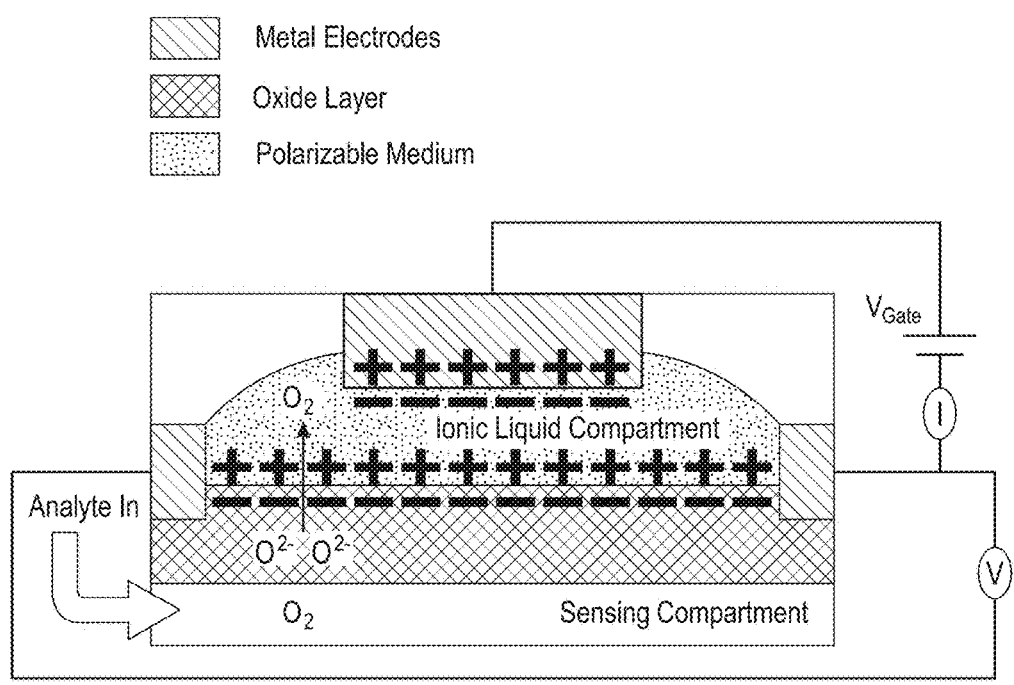
FIG. 8. A schematic (cross sectional view) of a first embodiment of the invention, which can be used as an oxygen sensor. The electrical conductance in the oxide layer is directly proportional to oxygen vacancy concentration in the oxide layer. The oxygen vacancy concentration can be controlled by varying either $V_{Gate}$ or the dissolved oxygen concentration in the analyte in the sensing compartment. At constant $V_{Gate}$, the oxide layer conductance is a direct measure of the concentration of the oxygen dissolved in the analyte in the sensing compartment. Electrons involved in the reaction are not shown.

FIG. 8 shows a first embodiment, an oxygen sensing apparatus that includes a chamber containing an ionic liquid (in its own compartment) and a second chamber (the "sensing compartment") containing the analyte. Between these two compartments is an oxide thin film, which is amenable to the creation of oxygen vacancies upon ionic liquid gating of the film. The creation of oxygen vacancies can be controlled by changing the oxygen concentration in the analyte. One method of sensing oxygen in the analyte is to measure the oxygen vacancy current (which is directly proportional to the charge current) through the oxide film. Equation 4 gives the relationship between the oxygen vacancy flux and oxygen vacancy concentration gradient.

$$J_v = -M_v \cdot C_v \cdot \left( R \cdot T \cdot \frac{d\ln C_v}{dx} + z_v \cdot F \cdot \frac{dV}{dx} \right) \quad (4)$$

Equation 4 shows that the vacancy flux, $J_v$, is directly proportional to the spatial gradient in the concentration of vacancies $$\left( \frac{d\ln C_v}{dx} \right),$$

which in turn is inversely proportional to oxygen concentration and the spatial gradient in the voltage $$\left( \frac{dV}{dx} \right).$$

Figure 1:
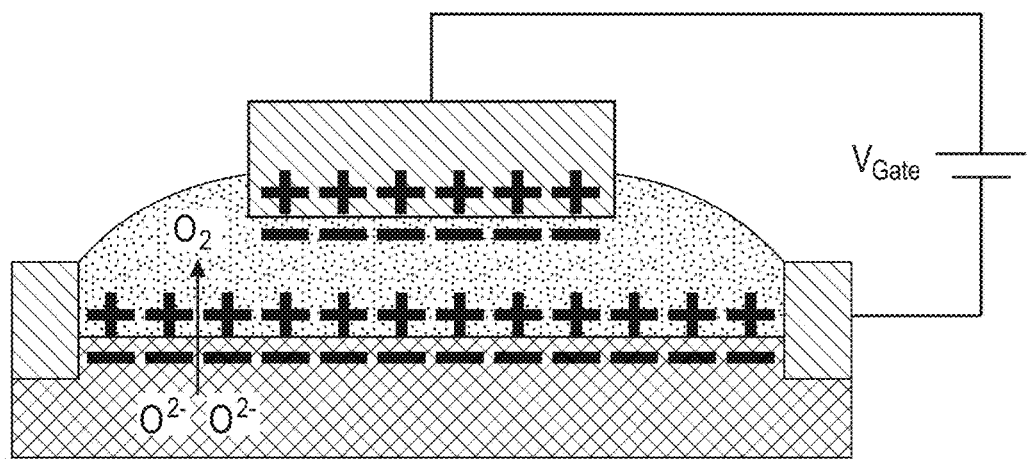
FIG. 1 illustrates the principle of ionic motion driven by a large electric field generated by an electrical-double layer.
Figure 2:
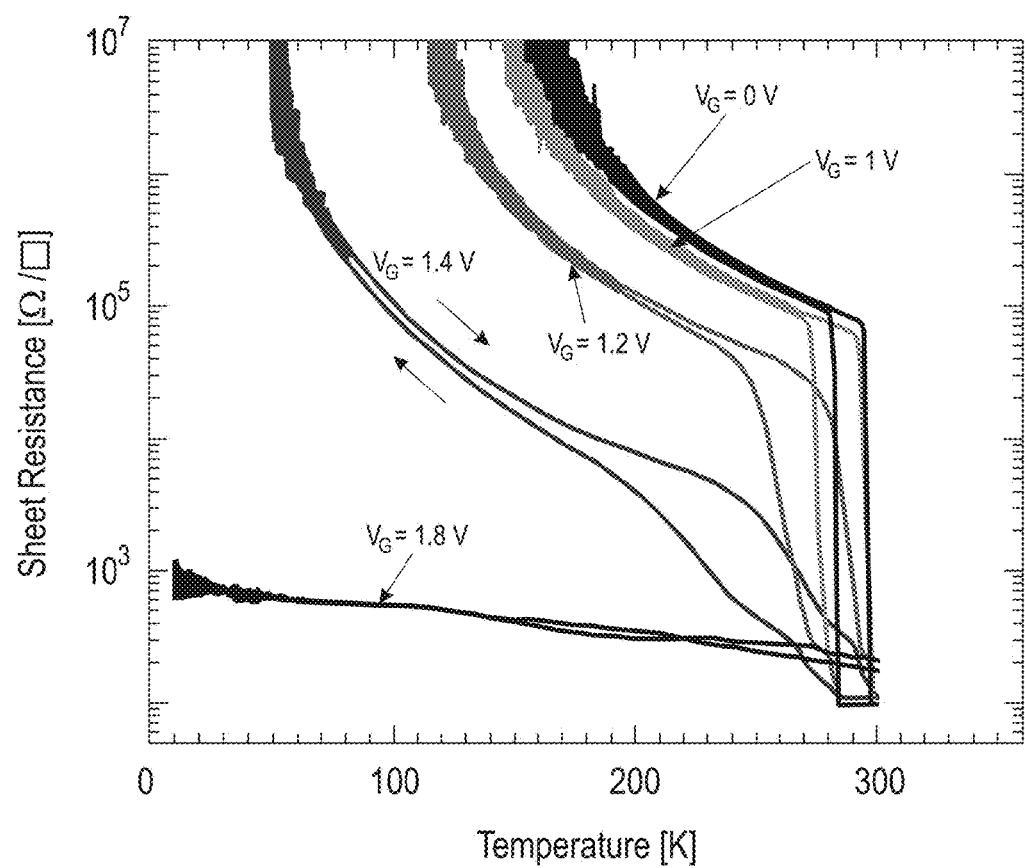
FIG. 2 illustrates ionic liquid gating induced MIT suppression in $VO_2/TiO_2$ films (taken from Jeong et al., supra).
Figure 3:
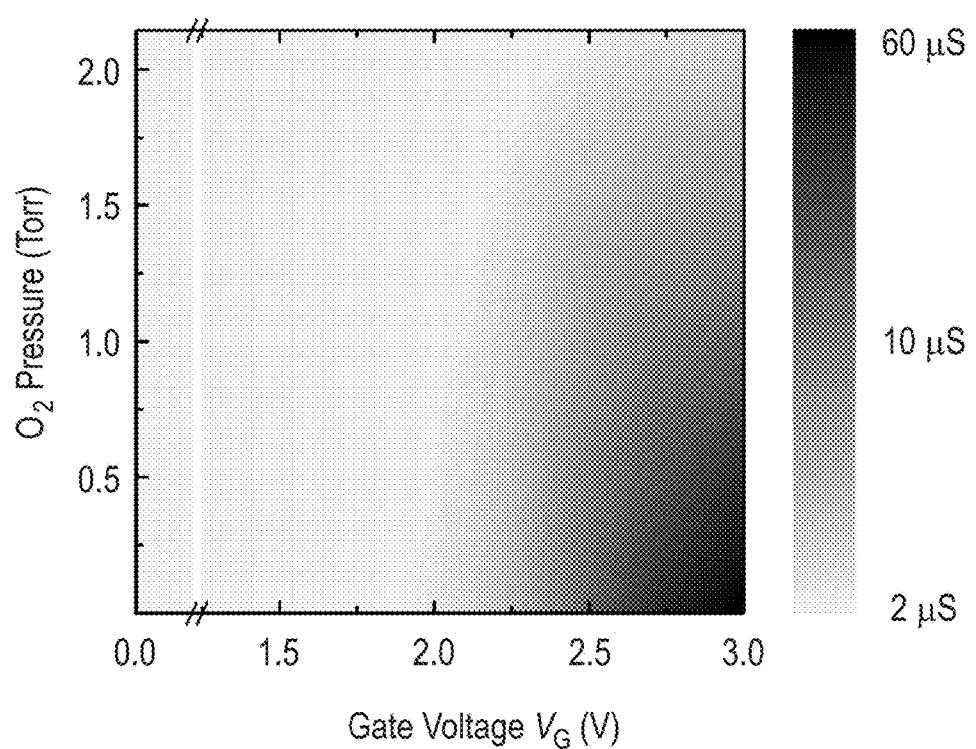
FIG. 3. The dependence of conductivity of ionic liquid gated $VO_2$ thin films as a function of oxygen pressure and gate voltage (taken from Jeong et al., supra).

In equation 4, $M_v$ corresponds to the mobility of oxygen vacancies, $C_v$ is the concentration of oxygen vacancies having a charge $z_v$, R is the universal gas constant, F is the Faraday constant, and T is the operating temperature. In this oxygen sensing device, a low oxygen concentration ($C_{O_2}{}^a$) is maintained in the ionic liquid in the ionic liquid compartment, while the oxygen concentration in the analyte (in the sensing compartment) is varied ($C_{O_2}{}^b$). The difference in oxygen concentration across the oxide film sets up an inverse gradient in the vacancy concentration, leading to a diffusive current which is indicative of the concentration of oxygen in the analyte. The magnitude of the diffusive current can be controlled by the gate voltage, as described by equation 4, and enables the sensitivity of the device to be dynamically changed. High gate voltages correspond to a large dynamic current range (see FIG. 3).

In a first step of operating the device, a gate voltage is temporarily applied to the ionic liquid in the ionic liquid compartment, e.g., as short as a few milliseconds. This results in the formation of oxygen vacancies in the thin oxide film that give rise to an increased conductivity in the thin oxide film. The conductivity of the oxide thin film is monitored using source and drain contacts (indicated by the metal electrodes on the far left hand side and the far right hand side in each of FIGS. 8 and 9). Depending on the oxide material that is used, the gate voltage can either be retained or switched off before the analyte is introduced into the sensing compartment. (For materials requiring the application of gate voltage of negative polarity to annihilate the oxygen vacancies, e.g., $VO_2$, the gate voltage can be switched off before the analyte is introduced. For materials exhibiting oxygen vacancy annihilation at zero gate voltage, the gate voltage must be retained.) When there is oxygen in the analyte, oxygen from the analyte enters the oxide channel, thereby reducing the number of oxygen vacancies and decreasing the conductivity of the oxide channel. The rate of conductivity decrease in the channel, as measured by the current between the source and drain electrodes at a small bias voltage applied between these same electrodes, is directly dependent on the oxygen content in the analyte. Faster conductivity relaxation is observed at higher oxygen concentrations.

In a second method, the time to reach saturation of the gate current (denoted "I" in FIGS. 8 and 9) is used to determine the oxygen concentration in the analyte. In this approach, a gate voltage is applied after the analyte is loaded into the sensing compartment. For constant gate voltage, the time required to attain saturation of the gate current is directly proportional to the oxygen concentration in the analyte. The necessary calibration can be made by considering the time scales to reach saturation at different, but known, oxygen concentrations. Two limiting calibration standards are (i) an analyte with essentially no dissolved oxygen and (ii) an analyte that is essentially saturated with oxygen, e.g., oxygen-saturated water.

Figure 9:
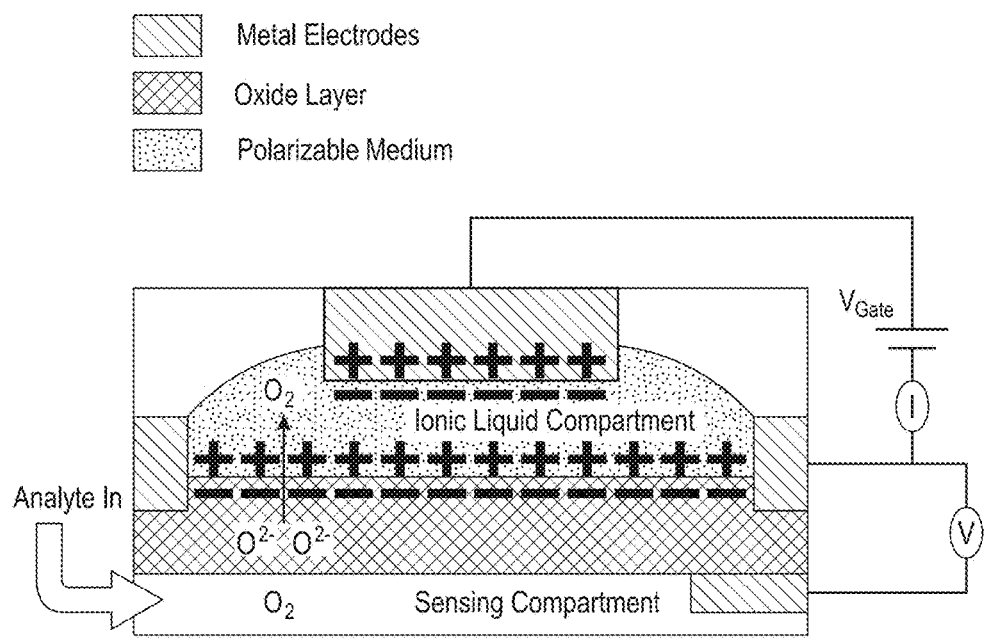
FIG. 9. A schematic (cross sectional view) of a second embodiment of the invention, which can be used as an oxygen sensor. The apparatus in FIG. 8 has been modified to measure the voltage drop across the thickness of the thin oxide film. The potential difference across the thin film can be used to sense concentration differences across the ionic-liquid gated thin oxide film.

A second embodiment for the measurement of a sense voltage across an oxygen deficient thin oxide film (in accordance with equation 5) is shown in FIG. 9. For this embodiment, a third method may be employed. First, oxygen deficiencies are created in the thin oxide film by applying a gate voltage to the ionic liquid, while maintaining the ionic liquid compartment at a low oxygen concentration. Next, the gate voltage is turned off and an analyte containing dissolved oxygen is introduced into the sensing compartment, to detect the oxygen concentration therein. This establishes an oxygen concentration gradient across the thin oxide film, which gives rise to a voltage difference, as given in equation 5.

$$V_b - V_a = \Delta V = \frac{RT}{4F} \ln \frac{C_{O_2}^a}{C_{O_2}^b} \quad (5)$$

For the above-described embodiments and methods, molecular oxygen (e.g., in air) is catalytically divided into two oxygen ions on the surface of the oxide film (facing the sensing compartment), ions which can then migrate through the oxygen ion transport channels present in the oxide film (facing the ionic liquid compartment), eventually making their way out of the oxide film. The oxygen ions then recombine at the interface between oxide film and the ionic liquid. (If the input gas contains species other than oxygen, such as nitrogen or argon, these other species are not transported through the oxide film, since the oxide film is impermeable to those species.) This is possible if there is sufficient electronic conductivity in the oxide film. The oxide film preferably has an electronic resistivity of <1 mΩ-cm when the electric field is applied via ionic liquid gating. Details regarding the catalytic processes leading to oxygen ions can be found in the reference Chueh et al., "Electrochemistry of mixed oxygen ion and electron conducting electrodes in solid electrolyte cells", Annual Rev. Chem. Biomol. Eng., vol. 3, pp. 313-341, 2012.

In FIGS. 8 and 9, an intense electric field is applied to the surface of the oxide thin film (facing the ionic liquid compartment), by using a polarizable medium (preferably an ionic liquid). The ionic liquid is polarized (leading to charge accumulation at the interface with the oxide film) by applying a voltage between (i) a gate electrode (here: located at the top of the device) that is in contact with the ionic liquid and (ii) a second electrode that is connected to the oxide film itself (here: connected to the right hand side of the oxide film). The gate electrode can be positioned in a number of places, provided that the ionic liquid covers both the gate electrode and the oxide film surface (facing the ionic liquid compartment). The gate electrode surface area is preferably at least as large as the surface area of the oxide film. The available surface area of the gate electrode may advantageously be enhanced by using a porous electrode structure. The gate electrode is positively biased with a voltage that both exceeds a minimum threshold voltage and is within the electrochemical stability window for the particular ionic liquid used. The ionic liquid can be chosen from a wide variety of ionic liquids that are both (i) liquid at the operation temperature of the device and (ii) stable to high potentials. Higher voltages and/or higher temperatures can be advantageously used to improve the sensitivity of the device. The operating temperature range will generally be limited to temperatures between the freezing point and the boiling point of the ionic liquid (polarizable medium).

Generally, any liquid into which oxygen can be dissolved may be considered for use as the analyte. This would include, for example, both water and blood. In the case of water, dissolved oxygen is an indicator of water quality. For example, excess nutrients in water promote the growth of phytoplankton in bodies of water, such as lakes. Over time, photosynthetic processes lead to an excess of oxygen. However, death and subsequent decomposition of phytoplankton lead to oxygen deficiency in the water. Therefore, monitoring the oxygen concentration in water is a way of assessing water quality and predicting the likelihood of eutrophication. In the case of blood, the amount of oxygen bound to hemoglobin is related to the health of an individual. Lower oxygen concentrations in blood can be an indication of unhealthy blood cells. This is because unhealthy blood cells have a low affinity for oxygen.

For FIGS. 8 and 9, the material for the oxide thin film is chosen from the class of oxide materials for which an electric field provided at the surface of the film causes migration of oxygen ions through the film. The electric field needs to be sufficiently intense that it results in the motion of oxygen ions. Such an intense field is advantageously provided herein by the use of a polarizable medium, such as an ionic gel (e.g., a mixture of a triblock copolymer, such as polystyrene-poly(ethylene oxide)-polystyrene, and an ionic liquid), a molten salt (e.g., single or multi-component salt mixtures, such as NaCl, optionally mixed with KCl), and/or an ionic liquid, although the latter is preferred. An ionic liquid in contact with the surface of the oxide membrane provides an intense electric field, when the ionic liquid is polarized by a small voltage applied across the liquid. Typical voltages that are required to polarize the IL are in the range of 1-3 V. The maximum voltage that can be applied to the ionic liquid depends on the so-called electrochemical stability window of the IL. Examples of useful ionic liquids include ethylmethylimidazolium bis(trifluoromethanesulfonyl)imide (EMIM-TFSI), butylmethylimidazolium bis(trifluoromethanesulfonyl)imide (BMIM-TFSI), hexylmethylimidazolium bis(trifluoromethanesulfonyl)imide (HMIM-TFSI), ethylmethylimidazolium trifluoromethanesulfonate (EMIM-triflate), butylmethylimidazolium trifluoromethanesulfonate (BMIM-triflate), hexylmethylimidazolium Trifluoromethanesulfonate (HMIM-triflate), ethylmethylimidazolium Tetrafluroborate (EMIM-BF4), butylmethylimidazolium tetrafluroborate (BMIM-BF4), hexylmethylimidazolium tetrafluroborate (HMIM-BF4), ethylmethylimidazolium hexafluorophosphate (EMIM-PF6), butylmethylimidazolium hexafluorophosphate (BMIM-PF6), hexylmethylimidazolium hexafluorophosphate (HMIM-PF6), and N,N-diethyl-N-(2-methoxyethyl)-N-methylammoniumbis (trifluoromethylsulfonyl)imide (DEME-TFSI).

The oxide material for the above-described embodiments and methods is preferably $VO_2$, $TiO_2$, $SrTiO_3$ and/or $WO_3$. These materials have a physical structure that includes channels for the passage of oxygen ions. $VO_2$ having a rutile structure is preferred, since it affords the highest oxygen conductivity along channels oriented along the compound's crystallographic c axis. The crystallographic framework of $VO_6$ octahedra that are edge-shared along the c axis, but corner-shared along the a and b crystallographic axes, gives rise to the observed anisotropic oxygen ion transport.

Similarly, other rutile oxides can be used, such as $TiO_2$. The dimensions of the channels perpendicular to the c axis vary with respect to the radius of the transition metal cation. For $TiO_2$, larger channels mean that oxygen can migrate more readily. $WO_3$ has a different crystal structure based on the cubic perovskite structure, with the nominal formula $ABO_3$ in which the A cations are not present in $WO_3$. $WO_6$ octahedra are corner-shared in all directions leading to open channels along all principal crystallographic axes. Other oxides with different crystal structures (but with channels along which oxygen ions can migrate under the application of sufficiently intense electric fields at the surface of the oxide) can also be used, e.g., greater than 10 MV/m.

For the embodiments shown in FIGS. 8 and 9, the devices can be prepared using microfabrication techniques, in which an oxide film is deposited onto a substrate (e.g., one selected to enable epitaxial growth) by physical vapor deposition. Most or all of this substrate may then be etched away (e.g., using dry or reactive ion etching), leaving an oxide film having two planar oxide surfaces. One of these surfaces faces the sensing compartment, while the other faces the ionic liquid compartment. (The analyte can be fed into the sensing compartment through a port. The same port, or a different port (not shown), may be used to remove the analyte from the sensing compartment.) The thickness of the oxide layer may be advantageously greater than 10 nm and less than 1 μm. The cross-sectional area of the planar surfaces can be advantageously chosen to control the sensitivity of the oxygen sensor, which is largely proportional to this cross sectional area (for a given polarizable medium).

The overall size of the described devices is related to the dimensions of the oxide film. For example, for the oxide films made for various test devices, the cross sectional area (facing the input or oxygen analyte) was on the order of 1 $mm^2$ to 1 $cm^2$. However, devices having larger cross sectional areas may also be easily fabricated, and would be advantageous in that they would permit the detection of even lower dissolved oxygen concentrations. Likewise, devices having smaller cross sectional areas may also be fabricated.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes within the meaning and range of equivalency of the claims are to be embraced within that scope.

The invention claimed is:

1. An apparatus, comprising:
   an oxide layer having ion transport channels therein, the channels facilitating the migration of oxygen ions from a first side of the layer to a second side of the layer;
   a first chamber having a polarizable medium located on the second side of the oxide layer;
   a second chamber having a liquid analyte that includes dissolved oxygen, the second chamber being located on the first side of the oxide layer; and
   a gate electrode that is in contact with, and applies a voltage to, the polarizable medium, such that an electric field is applied to the second side of the oxide layer, thereby driving oxygen ions across the oxide layer, so that oxygen ions travel from the first side of the oxide layer to the second side of the oxide layer, wherein:
   molecular oxygen is decomposed into oxygen ions at the first side of the oxide layer; and
   oxygen ions recombine into molecular oxygen at the second side of the oxide layer.

2. The apparatus of claim 1, wherein the oxide layer includes at least one of $WO_3$, $TiO_2$, $SrTiO_3$, and $VO_2$.

3. The apparatus of claim 1, wherein the oxide layer has an electronic resistivity of <1 mΩ-cm when the electric field is applied to the second side of the oxide layer.

4. The apparatus of claim 1, wherein the oxide layer has a thickness of greater than 10 nm and less than 1 μm.

5. The apparatus of claim 1, wherein the polarizable medium includes an ionic liquid.

6. The apparatus of claim 1, wherein the polarizable medium is an ionic liquid, an ionic gel and/or a molten salt.

7. The apparatus of claim 1, wherein the electric field is >10 MV/m.

8. The apparatus of claim 1, wherein the oxide layer and the chambers together form at least part of an oxygen sensor.

9. The apparatus of claim 1, wherein the polarizable medium includes an ionic gel.

10. The apparatus of claim 1, wherein the liquid analyte includes blood.

11. A method, comprising:
    using the apparatus of claim 1 to detect the concentration of oxygen in the analyte.

12. The method of claim 11, comprising using the apparatus at a temperature in the range between the freezing point and the boiling point of the polarizable medium.

13. The method of claim 11, comprising increasing the temperature of the oxide layer, thereby leading to enhanced oxygen detection sensitivity.

14. The method of claim 11, comprising increasing the voltage, thereby leading to enhanced oxygen detection sensitivity.

* * * * *